United States Patent [19]

Mehta et al.

[11] Patent Number: 4,944,894
[45] Date of Patent: Jul. 31, 1990

[54] ETHER FREE ORGANOMETALLIC AMIDE COMPOSITIONS

[75] Inventors: Vijay C. Mehta; Terry L. Rathman, both of Gastonia, N.C.; Ramiro Sanchez, Greenville, S.C.; Robert C. Morrison, Gastonia, N.C.

[73] Assignee: Lithium Corporatoin of America, Gastonia, N.C.

[21] Appl. No.: 160,229

[22] Filed: Feb. 25, 1988

[51] Int. Cl.$^5$ .............................................. C09K 3/00
[52] U.S. Cl. .............................. 252/182.12; 252/182.3
[58] Field of Search ........................ 252/182.3, 182.12

[56] References Cited

U.S. PATENT DOCUMENTS

| | | | |
|---|---|---|---|
| 3,742,077 | 6/1973 | Kamienski et al. | 260/668 |
| 3,822,219 | 7/1974 | Kamienski et al. | 252/431 |
| 3,847,883 | 11/1974 | Kamienski et al. | 260/837 |
| 4,139,490 | 2/1979 | Halasa et al. | 502/153 |

OTHER PUBLICATIONS

Ashby et al., J. Org. Chem., vol. 43, No. 8, 1978, p. 1564, *Reactions of Magnesium Hydrides.3.Stereoselective Reduction of Cyclic and Bicyclic Ketones by Dialkylaminomagnesium Hydrides.*
Houser et al., J. Am. Chem. Soc. 69, 295 (1947), *Condensation of Certain Esters by Means of Diethylaminomagnesium Bromide.*
Frostick et al., J. Am. Chem. Soc. 71, 1350 (1949), *Condensations of Esters by Diisopropylaminomagnesium Bromide and Certain Related Reagents.*
Bradley et al., Eur. J. Med. Chem. 115, 375 (1980), *Synthetic Studies on Meptazinol.Anion Chemistry in the Synthesis of α-Aryl Lactams.*
Ashby et al., J. Organometal. Chem. 14, (1968) 1–11, *Concerning The Purity of magnesium and Beryllium Alkyls and Halides Prepared by Different Methods.*
Joh et al., Macromolecules, vol. 3, No. 3, May–Jun. 1970, *Stereospecific Polymerization of Methyl Methacrylate by Organomagnesium Catalysts with A Magnesium–Nitrogen Bond.*
Kamienski, University Microfilms, Ann Arbor, Mich., Order No. 68-9810, pp. 59–60, *Synthesis and Properties of Diorganomagnesium Compounds.*
Kamienski et al., J. Org. Chem., vol. 30, p. 3498 (1965), *Relationship Between Structure and Solubility of Organic Lithium Compounds.*

Primary Examiner—Edward A. Miller
Attorney, Agent, or Firm—Charles C. Fellows; Robert L. Andersen

[57] ABSTRACT

An ether free magnesium bisorganoamide of the formula

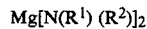

$$Mg[N(R^1)(R^2)]_2$$

wherein $R^1$ and $R^2$ are independently selected from hydrogen and alkyl groups containing 2 to 20 carbon atoms with the proviso that at least one of $R^1$ and $R^2$ is other than hydrogen or $R^1$ and $R^2$ taken together form an alkylene chain of 4 to 20 carbon atoms and a method of manufacture. Also disclosed are lithium-magnesiumorganoamides and organosubstituted lithium-magnesiumorganoamide.

4 Claims, No Drawings

ETHER FREE ORGANOMETALLIC AMIDE COMPOSITIONS

This invention concerns novel ether free organometallic amides and a process for their manufacture.

Organometallics have long been used in the preparation of pharmaceutical, agricultural and specialty chemicals. Metal amides have been frequently used to metallate a substrate as the nitrogen metal bond will react to replace an active hydrogen on a substrate and release the corresponding amine.

Organoamides of magnesium are useful metallating agents in chemical reactions. C. R. Hauser, H. G. Walker and F. C. Frastick, Jr., in J. Am. Chem. Soc. 69 295 (1947) and J. Am. Chem. Soc. 71 1360 (1949) reported use of bromomagnesiumdiethylamide and magnesium diisopropylamide to promote self-condensation of certain esters in diethyl ether. G. Bradley et al., in Eur. J. Med Chem 15 375 (1980) suggest that the so-called "Hauser Base" bromomagnesium diisopropylamide be considered as an alternative for lithium diisopropylamide in many of its numerous applications. The Hauser Base was prepared according to the Bradley et al., procedure and the product was a slurry. While slurries can easily be utilized when prepared in-house, hydrocarbon solutions rather than slurries are preferred commercial products for ease of use and wide acceptability.

Preparation of magnesium bisdialkylamides from dialkylmagnesium compounds and dialkylamines in tetrahydrofuran and other ethers is known (see Ashby, Lin and Goel, J. Org. Chem. Vol. 43, No. 8 pp 1564-1568, 1978). However, the users of magnesium bisdialkylamide compounds often desire ether free hydrocarbon solutions of the amides. Unfortunately, ethers are known to be quite difficult to separate from the lower dialkylmagnesium compounds and the downstream amides (see Concerning The Purity of Magnesium and Beryllium Alkyls and Halides Prepared By Different Methods by E.C. Ashley and R.C. Arnott J. Organometal. Chem. 14 (1968) 1-11 and Joh and Kataki in Macromolecular Vol. 3, No. 3, May-June 1970 report separating dioxane from a dialkylmagnesium.)

Hydrocarbon-soluble organometallic complexes of metals of Groups I and IIA of the periodic table are disclosed by C. W. Kamienski and J. F. Eastman in U.S. Pat. No. 3,742,077 and its divisional U.S. Pat. Nos. 3,822,219 and 3,847,883. Their means to achieving hydrocarbon solubility requires that at least one of the organometallic compounds involved be hydrocarbon-soluble while the other component may be hydrocarbon insoluble. Solubility does not occur when two insoluble components such as ethyllithium and diethylmagnesium are simply mixed together; the corresponding insoluble methyl compounds are even excluded from the scope of the invention.

There is a need for hydrocarbon soluble as well as insoluble ether free organometallic amides for use in organic synthesis; for example in preparation of alcohols from non-enolizable ketones and aldehydes. Ether free dialkylmagnesium compounds are known to react more efficiently with substrates in metallation reactions (University Microfilms, Ann Arbor, Mich., Order No. 68-9810 page 60). Since magnesium bisorganoamides are less nucleophilic than dialkylmagnesium but still strongly basic they have greater utility in metallation reactions. In cases where the divalency of the cation is important, magnesium metallating agents are needed for improved performance over monovalent lithium. Moreover, lithium diisopropylamide is known to have only limited solubility in hydrocarbons; for example only 0.2 normal in heptane (C. W. Kamienski and D. H. Lewis, J. Org. Chem. Vol. 30, p 3498, 1965). Whereas, the ether free magnesium bis(diisopropyl)amide of this invention has been found to be soluble to the extent of 1.4 normal in heptane.

The present invention provides novel, ether free, magnesium bisorganoamides and lithium-magnesiumorganoamides, a method of preparing them and bimetallic organoamides. The general method reacts two equivalents of an amine with a dialkylmagnesium compound in a liquid hydrocarbon solvent medium. The dialkylmagnesium compound must be ether free. Although at least one ether free dialkylmagnesium compound, a dibutylmagnesium compound (DBM) containing n-butyl- and s-butyl groups is commercially available, others can be produced in liquid hydrocarbon solvents and reacted with various amines such as dialkylamines, heterocyclic amines and so forth to produce magnesium bisorganoamides and other magnesium organoamides which are ether free. This is conveniently done in a liquid hydrocarbon solvent by reacting magnesium, preferably activated magnesium, with a suitable alkyl halide and reacting the resulting reaction product with an amine such as a dialkylamine to produce the desired magnesium bisdialkylamide. Generally reaction temperatures do not exceed about 100° C. or the solvent reflux temperature.

There are several process variations which can be employed to effect production of the desired magnesium bisdialkylamide compounds. These variations will be explained using as exemplary reactants n-butylchloride, n-butyllithium, diisopropylamine and activated magnesium. Those skilled in the art will recognize that other reactants can be employed in place of those listed here only for exemplary or explanatory purposes.

In accordance with one variation of the method of the present invention, two moles of n-butylchloride and two moles of activated magnesium are reacted in a liquid hydrocarbon solvent having a boiling point equal to or less than 100° C. to produce a di-n-butylmagnesium plus magnesium chloride product which may be a complex, and which precipitates. In the second step the di-n-butylmagnesium-magnesium chloride complex is reacted with two moles of diisopropylamine (DIPA) to yield two moles of chloromagnesium amide plus two moles of butane which leaves as a gas; this solid product may be a complex of magnesium bisdiisopropylamide and magnesium chloride. Chloromagnesium amide complex as a solid is also prepared in one step reaction by reacting activated magnesium metal with one mole of n-butyl chloride and one mole of diisopropylamine in hydrocarbon solvents such as hexane, cyclohexane, or heptane. The chloromagnesium amide or the complex product of the previous step is reacted with normal n-butyllithium to produce soluble n-butylmagnesiumamide plus solid lithium chloride. The major reaction product is a magnesium bisdiisopropylamide complexed with di-n-butylmagnesium. This product is also identified as n-butylmagnesium diisopropylamide (n-BuMg-N(iPr)$_2$); in the next step this reaction product is reacted with additional diisopropylamine to produce the magnesium bisdiisopropylamide product plus butane. This product is soluble so the lithium chloride can be removed by filtration. Should a lower boiling hydrocarbon be desired in the process, then diisopropylamine is advantageously added at the same time as the n-butylchloride in step 1 to lower the reaction temperature. It is thought that the diisopropylamine acts as a Lewis base in this reaction as well as a reactant. In like manner, diisopropylamine and n-butyllithium can also be added simultaneously to the chloromagnesium(organo)amide in step 3 to form magnesium bisdiisopropylamide.

A second process variation in accordance with this invention reacts two moles of n-butylchloride with two moles of magnesium to produce di-n-butylmagnesium plus magnesium chloride both of which are precipitated products (known in the art). The reaction product from step 1 is reacted with two moles of n-butyllithium to produce two moles of di-n-butylmagnesium plus two moles of lithium chloride which precipitates (known in the art). The reaction product of the second step, di-n-butylmagnesium plus lithium chloride, is reacted with two moles of diisopropylamine to produce magnesium bisdiisopropylamide plus butane; the lithium chloride, which is a solid, may be removed from this hydrocarbon soluble product. As was done in method 1, if desired, the diisopropylamine can be added simultaneously with n-butyllithium in step 2.

A third process variation in accordance with this invention reacts a mole of n-butylchloride and ethylchloride or n-hexylchloride or n-octylchloride with two moles of magnesium to produce a hydrocarbon soluble mixed dialkylmagnesium plus magnesium chloride which precipitates (known in the art). Magnesium chloride is filtered off after which the mixed dialkylmagnesium is reacted with two moles of diisopropylamine to form the desired magnesium bisdiisopropylamide plus two moles of a mixed alkane. It is possible to leave the magnesium chloride in the reaction medium during the reaction with diisopropylamine but as in process variation 1, insoluble chloromagnesiumamide is formed which requires extra steps for conversion to magnesium bisdiisopropylamide.

A fourth process variation in accordance with this invention reacts two moles of n-butylchloride with two moles of magnesium to produce a mole of di-n-butylmagnesium plus magnesium chloride which precipitate as solids (known in the art). The second step of this variation reacts the di-n-butylmagnesium and magnesium chloride with two moles of secondary butyllithium to produce two moles of hydrocarbon soluble n-butyl, s-butylmagnesium plus two moles of lithium chloride which precipitates and can be removed by filtration (known in the art). The n-butyl-s-butylmagnesium is then reacted with two moles of diisopropylamine to form magnesium bisdiisopropylamide plus two moles of butane. On reaction of the n-butyl-sec-butyl magnesium with only one mole of the amine, a hydrocarbon soluble composition (represented by RMgN(iPr)$_2$) is formed. Other commercially available dialkylmagnesium compounds, such as n-butylethylmagnesium (BEM) and n-butyloctylmagnesium (BOMAG ™) may be substituted for the n-butyl-sec-butylmagnesium.

The various illustrated processes are not restricted to producing hydrocarbon-soluble magnesium bis-(secondary amides) but can also be applied successfully to production of other insoluble analogs. Included among such insoluble secondary magnesium amide compounds are for example magnesiumbis(diethyl)amide, magnesium bispyrrollidide. Also contemplated are insoluble primary magnesium bisalkylamides such as magnesium bis(isopropyl)amide, magnesium bis(2-ethylhexyl)amide and magnesium bis-(2,2-dimethyl-1-propyl)amide. Table 1 contains a list of representative compounds.

Also contemplated are intermediates in the above process of manufacturing the magnesium bis(organo)amides, such as, e.g., halomagnesium(organo)amides, particularly chloromagnesium diisopropyl amide, and also alkylmagnesium(organo)amides such as, e.g., n-butylmagnesium diisopropylamide and sec-butylmagnesium(organo)amides.

The reaction of a diorganomagnesium compound with a diorganoamine in accordance with the present invention can be represented by the reaction equation $$R^1R^2Mg + 2R^3R^4NH \rightarrow Mg(NR^3R^4)_2 + R^1R^2$$

wherein $R^1$, $R^2$, $R^3$ and $R^4$ are independently selected from hydrogen, primary, secondary and tertiary alkyl and cycloalkyl groups containing 2 to 20 carbon atoms and aryl groups containing 6 to 10 carbon atoms. When less than two moles of amine are used per mole of diorganomagnesium compound the alkylmagnesium organoamide produced can be represented by the formula $$R^1_x Mg(NR^3R^4)_{2-x}$$

wherein $R^1$, $R^3$ and $R^4$ have the meanings hereinbefore ascribed to them and x is equal to or greater than 0.1 and less than 2. These latter compounds, alkylmagnesium organoamides such as n-butylmagnesium diisopropylamide, s-butylmagnesium diisopropylamide and so forth are known to be useful in the manufacture of catalysts used in the polymerization of rubber.

The first process variation discussed above involves reaction of diisopropylamine in two stages whereas process variations 2, 3 and 4 involve only single additions of diisopropylamine. Process 3, however, can also be operated like process 1 if the magnesium chloride is not filtered off in step 1. Then additional steps are necessary in order to convert the insoluble complex (chloromagnesiumamide) through further reactions with either normal or secondary butyllithium to form an alkylmagnesium dialklamide followed by reaction with additional diisopropylamine to form the desired magnesium bisdiisopropylamide.

It is known that alkali metal organoamides, such as lithium diisopropylamide (LDA) are insoluble of themselves in purely hydrocarbon solvents at ordinary temperatures. It has now surprisingly been found that hydrocarbon-insoluble LDA can be made soluble in ether-free hydrocarbon solutions by the addition of magnesium bisdiisopropylamide, even in those cases where the lithium to magnesium ratio is significantly greater than one.

This aspect of the invention concerns bimetallic amide compositions, termed here lithium magnesium diorganoamides, which may be represented by the formula $$Li_x Mg_y(NR^3R^4)_z$$

wherein $R^3$ and $R^4$ have the meaning ascribed to them herein above, $x+y=1$ and $z=x+2y$. In specific examples, the compounds $Li_{0.01}Mg_{0.99}(NR^3R^4)_{1.99}$ and $Li_{0.99}Mg_{0.01}(NR^3R^4)_{0.01}$ represent opposite ends of the mole fraction range for Li and Mg. The maximum value for z is thus 2.0 and the minimum value for z is 1.0, and these values occur only when the pure compounds $Mg(NR^3R^4)_2$ and $LiNR^3R^4$, respectively, would be present. Compositions with high lithium levels are useful as metallating agents and compositions high in magnesium are useful as alkylating agents. These bimetallic organoamides are usefully dissolved in the same liquid hydrocarbon solvents as the magnesium bisorganoamides of this invention.

A $Li_{0.9}Mg_{0.1}(N(iPr)_2)_{1.1}$ product was found to be soluble in pure cyclohexane to the extent of an overall amide $(N(iPr)_2)$ concentration of 1.43 moles per liter at ordinary temperatures. It was found that variation of the Li/Mg ratio in these mixed diisopropylamides between 0.1-10 did not improve the solubility beyond the level of about 1.5 moles of amide/liter, which product solutions were not stable to precipitation for longer than a few days at ambient or room temperatures.

Magnesium bisdiisopropylamide/lithium diisopropylamide mixtures are soluble up to about 90% lithium diisopropylamide with 10% added magnesium bisdiisopropylamide, but the maximum solubility does not exceed the total amide solubility of about 1.4 to 1.5 moles per liter. Interestingly, lithium diisopropylamide's solubility is maintained in the presence of magnesium bisdiisopropylamide in such hydrocarbon solvents in the absence of ethers for limited periods of time, even at cold temperatures.

Such hydrocarbon-soluble bimetallic lithium magnesium diisopropylamides are readily prepared by slow addition (with cooling) of an alkyllithium compound, such as n-butyllithium, dissolved in a hydrocarbon solvent such as cyclohexane, to a solution of magnesium bisdiisopropylamide in cyclohexane, containing diisopropylamine in a quantity equivalent to the n-butyllithium being added.

When a lesser quantity of an organoamine is present in the above mixture than is necessary to react with all of the alkyllithium being added, then hydrocarbon-soluble ether-free organosubstituted lithium magnesiumorganoamides are produced which can be represented by the formula $$Li_xMg_yR^1{}_a(NR^3R^4)_b$$

wherein $R^1$, $R^3$ and $R^4$ have the meaning ascribed to them herein above, $x+y=1$ and $a+b=x+2y$.

These compositions can also be formed by direct admixture of an alkyllithium and magnesium bisorganoamide or admixture of a dialkylmagnesium and lithium organoamide.

Surprisingly, it has also been discovered that, even in the absence of any magnesium diorganoamide ($y=$zero in above formula), reaction of alkyllithium with less than a stoichiometric amount of diorganoamine leads to the formation of hydrocarbon soluble organolithium/lithium organoamide compositions represented by the formula $$(LiR^1)_x(Li(NR^3R^4))_y$$

or, as above,
$$Li_xR^1{}_a(NR^3R^4)_b$$

wherein $R^1$, $R^3$ and $R^4$ have the meaning ascribed to them herein above, and $a+b=x$. These compositions have been found to be quite stable relative to ether-containing solutions of lithium organoamides.

The products of this invention are prepared from numerous different amine types of the formula $$R_xNH_y$$

and includes the following depending on the values assigned to x and y:

1. Amine types where $x=2$ and $v=1$ — These are $C_2$–$C_{20}$ dialkylamines (secondary amines) such as dimethylamine, diethylamine, di-n-propylamine, diisopropylamine, di-n-hexylamine, dicyclohexylamine, and isopropylcyclohexylamine, diphenylamine, phenylisopropylamine, and phenyl-n-butylamine.

2. Amine types where $x=1$ and $v=1$ — These are cycloalkyleneimines (secondary amines) such as tetramethyleneimine, common name = pyrrollidine; pentamethyleneimine, common name = piperidine; and the like in which the R group is a diradical; that is, possesses two points of attachment to nitrogen. Included among such R groups are those cycloalkylene radicals possessing a hetero atom, either in the chain itself such as for example the ethyleneoxyethyl diradical (common name for this amine is morpholine), or as part of a radical attached to the cycloalkylene moiety such as the 2-methoxytetramethylene diradical (common name for this amine is 2-methoxypyrrollidine). Included in this type are lower alkyl disubstituted compounds such as 2,5-dimethylpyrrolidine, 2,6-dimethylpiperidine and the like.

3. Amine types where $x=1$ and $v=2$ — These are monoalkylamines (primary amines) such as methylamine, ethylamine, n-propylamine, 2-ethylhexylamine, and isopropylamine, aniline, and toluidine.

The products made from lower dialkylamines tend to be hydrocarbon insoluble but it was found that amines containing secondary alkyl groups such as diisopropylamine are hydrocarbon soluble. Similarly the $C_5$ and $C_6$ cyclic amines are hydrocarbon insoluble but products of the invention made from lower alkyl substituted cyclicamines such as 2,2,6,6-tetramethylpiperidine and 2,6-dimethylpiperidine are hydrocarbon soluble. Products made from longer straight chain amines such as di-n-hexylamine tend to be soluble but surprisingly products made from dicyclohexylamine are not soluble in hydrocarbon solvents.

The magnesium metal, when used in this method, is preferably activated by heating the metal at the atmospheric reflux temperature of the hydrocarbon selected as the reaction medium in the presence of a small amount of iodine for about 60 minutes in an inert atmosphere. This and other magnesium activation techniques are well known in the art. The amount of iodine employed and treatment time and temperature can vary a great deal. The magnesium can be in any form but to facilitate the reaction with the alkyl halide they are preferably used in powder or chip form.

The alkyl halide used to react with magnesium metal is selected from $C_1$ to $C_{20}$ alkyl halides in which the halide is bromine, chlorine or iodine. The $C_1$ to $C_8$ alkyl halides are preferred and $C_1$ to $C_4$ alkyl halides are most preferred because in the process the alkyl group is removed as an alkane and the gaseous alkanes are easiest to remove from the reaction medium.

The inert liquid hydrocarbon solvent employed in the method of the invention can be selected from many inert liquid hydrocarbon solvents such as n-hexane, cyclohexane, n-heptane, methylcyclohexane, isoparafinic solvents such as Isopar TM E, G or H with n-heptane and cyclohexane being preferred. Aromatic solvents may also be employed, for example toluene or xylene.

The organolithium used in the method of the invention is selected from $C_1$ to $C_{20}$ preferably $C_1$ to $C_8$ alkyl-, cycloalkyl- and aryllithium compounds and most preferably from n-butyllithium, s-butyllithium and t-butyllithium.

The following examples further illustrate the invention. All examples using lithium and/or magnesium metals were conducted under an argon atmosphere.

EXAMPLE 1: MAGNESIUM BISDIISOPROPYLAMIDE IN CYCLOHEXANE

Magnesium metal chips (6.0 gms, 0.247 mole), 0.10 gm iodine crystals and 200 mls of pure cyclohexane were charged into a glass reactor under argon atmosphere. The metal slurry was heated to reflux temperature (80° C.) and stirred for sixty minutes at reflux for activation of metal. n-Butyl chloride (26 mls, 0.25 mole) was then added to the metal slurry at reflux temperature over a period of twenty minutes. Reflux temperature dropped to 78° C. and a slow reaction was observed. Next, 35 mls (0.25 mole) of diisopropylamine was added to reflux temperature; within a few minutes, butane started refluxing and depressed reaction temperature to 60° C.

Heating was cut off, and the vigorous reaction continued at below the reflux temperature. The reaction was completed at 55° C.-60° C. in about three hours, and almost all metal chips had been converted into a fine white solid product in cyclohexane solvent. Next, the slurry was allowed to settle, and the clean solution was tested for soluble magnesium. No soluble magnesium was found. To this slurry n-butyllithium (no more than 0.247 mole) was added at 20°-25° C. with good agitation. The reaction was continued for sixty minutes at 25° C. (controlled temperature), and then 43 mls of diisopropylamine was added to the reaction slurry. Stirring was continued for an additional sixty minutes before it was filtered to remove solids. About 400 mls of clear filtrate was obtained. Solid and filtrate samples were analyzed. The analysis of the liquid was found to contain 0.5M concentration of magnesium bisdiisopropylamide, 20 ppm Li, and 60 ppm chloride. The solid was mainly LiCl along with some unreacted magnesium and undissolved amide. The recovery (yield) of magnesium in the solution product was close to 90% including handling and entrainment loss.

COMPARATIVE EXAMPLE (Yasushi Joh and Yahide Katake; Macromolecules Vol. 3, No. 3, May-June 1970)

PREPARATION OF Et$_2$Mg-DIOXANE COMPLEX

Diethylmagnesium-dioxane complex was prepared according to the Schlenk procedure (W. Schlenk and W. Schlenk, Jr., Ber., 62B, 920 (1920); 64B, 734 (1961) and Walter Strohmier and Friedrich Seifert, Chem. Berichte, 94 2357 (1961).

7.0 gm (0.288 moles) magnesium chips are reacted with ethyl chloride (0.288 moles) in 250 mls of diethylether at reflux temperature to form Grignard solutions. The reaction product was then filtered to obtain clean solution of Grignard and removed are insoluble solids containing unreacted metal. The Grignard solution was dripped slowly into a boiling (refluxing) mixture of 120 mls of dioxane and 600 mls of diethylether. Finally, the reaction mixture is refluxed for 8 hours with stirring, and after cooling, is filtered to obtain clear solution of Et$_2$Mg-dioxane complex. The solid removed is essentially MgCl$_2$-dioxane complex. The clear solution was made up to 1000 mls and the concentration of magnesium was found to be 0.10 molar. Then 1000 mls of clean solution was divided into two round bottom flasks (each having 500 mls).

ISOLATION OF Et$_2$Mg

The Et$_2$Mg-dioxane solution in diethylether of both flasks were concentrated first by distillation of ether at atmospheric pressure with the aid of a condenser. When no more ether comes over, the flasks were connected to a high vacuum apparatus first at low temperature and then slowly increasing to 60° C. to pull off the rest of the ether and some dioxane. At this point product in both the flasks turned to whitish crystalline solid. Finally, the vacuum is increased to full and the flasks heated in oil bath at 120°±1° C. for 30 hours. The splitting off of dioxane was seen for a few hours. The solid sticks to the wall of the flask up to the neck area. Precaution was taken to keep the flask under oil bath at 120° C. up to the top of the neck. After 30 hours of heating at 120° C., both the flasks were filled with argon and removed from the vacuum apparatus.

REACTION OF IOSLATED Et$_2$Mg SOLID WITH AMINE

Flask #1 — The white solid was washed with n-heptane three times with the aid of a magnetic stirrer. The washing with n-heptane would help to dissolve dioxane if any present. The washed solid was then reacted with 100 mls mixture of 85 mls of n-heptane containing 15 mls (0.107 moles) of diisopropylamine. The reaction mixture after 15 minutes of stirring found to contain suspended fine white solids. The suspended solids were allowed to settle down and clean solution was analyzed and found to contain 0.30 molar concentration of magnesium and G.C. analysis showed the presence of less than 1.0 mole percent based on magnesium are dioxane and ether. Results showed loss of Mg as solid approximately 30 to 40%. This solid is comprised of magnesium amide chloride complex and/or MgCl$_2$ complexed with traces of dioxane and/or decomposed product.

Flask #2 — The white solid was reacted with a mixture of 85 mls of toluene and 15 mls of didiisopropylamine with the help of a magnetic stirrer under argon atmosphere. After 15 minutes of reaction, the reaction mixture was found to contain some fine fluffy suspended particles which were allowed to settle and clear solution was analyzed, and found to contain 0.38 molar concentration of magnesium and G.C. analysis indicated the presence of less than 1.0 mole percent on magnesium basis, are dioxane and diethylether. Result showed the loss of 24% of the magnesium in the solid. Solid material is magnesium amide halide complex and/or MgCl$_2$ and/or decomposed product.

OBSERVATION (i) Over all yield of magnesium as magnesium bisdiisopropylamide is between 25 to 35% of the starting magnesium.

(ii) Processing time is too lengthy, costly and not possible to commercialize.

(iii) On a larger scale there is no guarantee of 100% removal of dioxane by heating at 120° C. under reduced pressure.

EXAMPLE 2: REACTION OF ETHER FREE DIALKYLMAGNESIUM (DBM) IN N-HEPTANE WITH DIPA 165 gms of 20.8 wt percent concentration DBM in n-heptane (containing 0.2345 moles of Mg) was charged into a reaction flask under argon atmosphere. 34 mls (0.242 mole) of diisopropylamine was then added drop by drop to the DBM. Reaction temperature was rising due to the exothermic reaction. Temperature of the reaction flask was controlled at 25° C. by outside cooling. Sample #1 was drawn from the reaction flask after 10 minutes of stirring for NMR analysis. The reaction slurry was then heated to reflux (63° C.) for 10 minutes and another sample #2 was drawn for NMR analysis. Samples #1 and 2 were taken for NMR analysis to find out the nature of reaction at 25° C. and at reflux temperature when DBM to DIPA reaction was carried out at a 1:1 mole ratio.

The same reaction llask was then cooled down to 25° C. and then was added to it 34 mls of DIPA (0.242 mole) under controlled conditions. Sample #3 was drawn for NMR analysis. Then the reaction flask was heated to reflux (50° C.) for 10 minutes and sample was drawn for NMR analysis.

RESULTS (i) NMR spectra of Samples #1 and 2 indicated very clearly that 50% of the DBM was reacted with DIPA when 1:1 mole ratio used.

(ii) NMR spectra of samples #3 and 4 indicated no DBM left unreacted where 2 mole DIPA added per mole DBM.

(iii) Reaction temperature seen rising when second mole of DIPA was added.

(iv) Reflux temperature dropped to 52° C. from 63° C. when second mole of DIPA was added (due to the release of butane).

EXAMPLE 3: CONVERSION OF BENZOPHENONE TO BENZHYDROL USING MAGNESIUM BISDIISOPROPYLAMIDE

The reductions presented here are illustrated by the procedure for the conversion of benzophenone to benzhydrol. Thus, 4.56 g (25 mmol) of benzophenone were placed in a 100 ml airless-ware (R) flask and then 50 ml of a 0.5 magnesium diisopropylamide solution (in cyclohexane) were added slowly over a 10 min. period while maintaining the flask under an inert-gas atmosphere. The reaction mixture was then heated at reflux for 4 h. The resultant product mixture was cooled to room temperature and then hydrolyzed with 20 ml of a deoxygenated 2N HCl solution. The hydrolyzate was extracted thrice with ether and the ether extracts were combined, dried and finally submitted to solvents removal under reduced pressure yielding benzhydrol as a solid 3.2 g (70%). The physical and spectral data recorded on the product confirmed that it was benzhydrol.

EXAMPLES 4-23: REACTION OF ETHER FREE DIALKYLMAGNESIUM (DBM) IN HYDROCARBON SOLVENTS WITH VARIOUS AMINES 20 mls of dibutyl (n-butyl-sec-butyl) magnesium in n-heptane or n-hexane having 0.72 and/or 1.00 molar concentration was charged into each reaction test tube under an argon atmosphere. Then at least two moles of each amine per mole of magnesium were added drop by drop into their designated reaction test tubes. Throughout the addition of the amine, it was noted that soluble compositions representing alkyl magnesium amides $RxMg(NR'R'')_{2-x}$ are formed throughout as the reaction proceeds. Reaction temperature rose due to the exothermic reaction, and was controlled at below 25° C. by external cooling. After completion of the reaction, all test tubes were tested for soluble magnesium and stability of solution at room temperature and below for 24 hours. Results of these tests and amounts of reactants employed are shown in Table 2.

EXAMPLE 24: MAGNESIUM BIS-DI-N-HEXYLAMIDES IN CYCLOHEXANE

Magnesium metal chips (12.5 gms, 0.514 mole), 0.25 gm iodine crystals and 250 mls of pure cyclohexane were charged into a one liter reaction flask, under argon atmosphere. The metal slurry was heated to reflux temperature (80° C.) and stirred for sixty minutes at reflux for activation of metal. 52 mls (0.495 mole) of n-butyl chloride was then added to the metal slurry at reflux temperature over a period of 20 minutes. Reflux temperature dropped to 78° C. and no vigorous reaction was observed. Next, 120 mls (0.514 mole) of di-n-hexylamine was added at reflux temperature, within a couple of minutes, reaction was started vigorously with the release of free butane. Reflux temperature started dropping with the addition of amine. Most of the time during addition of amine, heating was cut off and reaction temperature was maintained close to reflux. The reaction was completed in about three hours at reflux temperature (50°-55° C.). Almost all metal chips had been converted into reaction products. At the end the reaction slurry turned thick, viscous, containing white solids, and found not filterable or syringeable. Next the slurry was allowed to settle for obtaining clean solution on the top, but did not work because it was too viscous for solid to settle down at the bottom. Finally 58.0 mls (0.25 mole) di-n-hexylamine and 50 mls of cyclohexane were added to thin out and then filtered at 30°±35° C. Filtration rate was good. Filtrate was clear, yellow in color, free from halide and had 0.60 molar magnesium concentration (as magnesium bis di-n-hexylamide). Solid white insoluble on filter was primarily $MgCl_2$ containing a few unreacted excess metal particles.

EXAMPLE 25: PREPARATION OF MAGNESIUM BIS-DI-N-BUTYLAMIDE 6.51 gm (0.267 mole) magnesium metal chips; 0.15 gm iodine crystals and 200 mls of n-heptane were charged into a one liter reaction flask under argon atmosphere. The metal slurry was heated to reflux for 60 minutes for activation of metal. 26 mls (0.25 mole) of n-BuCl and 42 mls (0.25 mole) of di-n-buitylamine were added to the metal slurry over a period of one hour. During this period heating was cut off. The reaction temperature was maintained very close to reflux. The reflux temperature was dropping continuously with the release of butane. Finally the reaction was allowed to run for three hours at reflux temperature (55°-60° C.) until almost all metal chips had been converted into a fine white solid insoluble product in heptane. Next, slurry was allowed to settle and clean solution was tested for soluble magnesium and found none. To this slurry 112.5 ml (0.225 mole) n-butyllithium was added at 30° C. with good agitation. After 60 minutes of stirring, 42 mls (0.25 mole) di-n-butylamine was added to the reaction slurry. The slurry was filtered after 30 minutes of stirring, to remove solid mainly consisting of LiCl along with unreacted metal, undissolved amide complex, and obtain filtrate as soluble magnesium bis-di-n-butylamide in heptane. The solution product (350 mls approx.) had a light yellow color and 0.68 molar magnesium and 1.36 molar active amide concentration.

EXAMPLE 26: $Li_{0.33}Mg_{0.67}(NR_2)_{1.67}$

Ether-free cyclohexane soluble magnesium bisdiisopropylamide (75 mls. 0.0375 moles) was first charged into a reaction flask under argon atomsophere, followed by adding to it 3.0 mls (0.02143 mole) diisopropylamine. This solution was then reacted with dropwise addition of 9.0 mls (0.018 mole) n-butyllithium in cyclohexane at low temperature (10° C.) using cooling bath. Release of free butane during addition of butyllithium was seen. A clear solution of the product, without forming any solid, was obtained. The reaction product as a soltuion remained clear for a couple of days. The analysis of the solution showed the presence of Li=0.21 M, Mg=0.43 M, amide=1.07 M, excess (free) amine=0.03 moles/mole amide.

EXAMPLE 27: $Li_{0.50}Mg_{0.50}(NR_2)_{1.50}$

The above Example 26 was repeated as described above, and then 3.0 mls (0.02143 mole) of additional diisopropylamine was added first followed by the addition of 9.0 mls (0.018 mole) of n-butyllithium at <1.0° C. The reaction mixture was stirred well at low temperature and then at room temperature. No solid was formed. The clean solution product was found to be stable between 0° C. and room temperature for at least one day. The analysis of the product showed the presence of Li=0.36 M, Mg=0.38 M, amide=1.12 M, excess (free) amine=0.06 mole/mole of amide.

EXAMPLE 28: $Li_{0.67}Mg_{0.33}(NR_2)_{1.33}$

The above Example 27 was repeated as described above, and then 6 mls (0.04285 mole) of diisopropylamine was added to it followed by adding 18 mls (0.036 mole) of n-butyllithium at <10° C. under good agitation. The reaction mixture was stirred at room temperature for some time. A clear solution free of any solid product at room temperature was obtained. The solution product did form solid (precipitation) at <10° C. on cooling for some time. The analysis of this product showed the presence of Li=0.58M, Mg=0.305, amide=1.20 M, excess (free) amine =0.09 mole/mole amide.

EXAMPLE 29: $Li_{0.67}Mg_{0.33}(R)_{0.33}(NR^1_2)_{1.0}$

The above Example 28 was repeated as described except that, instead of the total amount of diisopropylamine being present as shown along with magnesium bisdiisopropylamide (MDA) a smaller quantity of only 0.054 moles of diisopropylamine is admixed with the MDA. A clear solution resulted.

Alternatively, 38.0 ml of 1.7N n-butyllithium in heptane was reacted with 4.25 ml (0.03 mole) of diisopropylamine and then 50 ml of 0.6M (0.03 mole) magnesium bisdiisopropylamide added to give a clear solution.

EXAMPLE 30: SYNTHESIS OF A SOLUBLE n-BUTYLLITHIUM/ LITHIUM DIISOPROPYLAMIDE COMPOSITION (50/50 MOLE %) IN CYCLOHEXANE (NO LEWIS BASE)

This experiment shows that a highly soluble, Lewis base free composition of n-butyllithium/lithium diisopropylamine composition (50/50 mole %) which is more thermally stable than LDA solutions in THF can be synthesized.

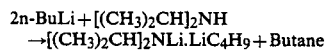

A 100 ml bottle was dried in an oven (150° C.), purged with argon and then equipped with a rubber septum. Next, n-butyllithium (0.098 mole) in cyclohexane was added to the bottle via syringe. Dry diisopropylamine (0.49 mole) was then added dropwise, also by syringe, over a period of 10 minutes. The bottle and contents became warm (40° C.) due to the formation of lithium diisopropylamide and butane. The product solution was cooled to about 25° C. The final product (W.E. titration =1.70 M) was slightly yellow, clear and contained no solids indicating the n-BuLi/LDA complex to be quite soluble. This composition was determined to be nonpyrophoric as compared to 16 weight % n-butyllithium in cyclohexane. The product solution was placed in the refrigerator (3°±3° C.) and after five days precipitation occurred (white crystals). These crystals redissolved on warming. GLC analyses indicated the product to be a 50/50 mole % composition of n-butyllithium/lithium diisopropylamide.

COMPARATIVE EXAMPLE 30: SYNTHESIS OF LITHIUM DIISOPROPYLAMIDE IN CYCLOHEXANE (NO LEWIS BASE)

Example 30 was repeated except that n-butyllithium (0.037 mole) in cyclohexane was reacted with diisopropylamine (0.037 mole). The final lithium diisopropylamide product contained solids and was very, very viscous like a glass.

EXAMPLE 31: SYNTHESIS OF A SOLUBLE s-BUTYLLITHIUM/ LITHIUM DIISOPROPYLAMIDE COMPOSITION (50/50 MOLE %) IN CYCLOHEXANE (NO LEWIS BASE)

EXAMPLE 30 was repeated except that s-butyllithium (0.036 mole) in cyclohexane was employed to react with diisopropylamine (0.18 mole). The resultant 1:1 s-butyllithium/lithium diisopropylamide complex product solution was completely soluble in cyclohexane (W.E. titration=1.31 N), contained no precipitate, and was non-viscous. After 42 days in the refrigerator (3°±3°C.) this product solution remained clear (no precipitation).

EXAMPLE 32: SYNTHESIS OF A SOLUBLE s-BUTYLLITHIUM/ LITHIUM DIISOPROPYLAMIDE COMPOSITION (33/67 MOLE %) IN CYCLOHEXANE (NO LEWIS BASE)

Example 30 was repeated except that s-butyllithium (0.037 mole) in cyclohexane was reacted with diisopropylamine (0.025 mole). The resultant 1:2 ,s-butyllithium/lithium diisopropylamide complex was completely soluble in cyclohexane (W.E. titration=1.33 M) and contained no precipitation. The final product was slightly viscous. After 21 days in the refrigerator (3 °±3° C.) the product solution contained no precipitation.

TABLE 1

Representative Compounds
$[R^1R^2N]Mg[NR^1R^2]$

| Comp. No. | Compound Type | $R_1$ | $R_2$ |
|---|---|---|---|
| 1 | Secondary | $CH_3$ | $CH_3$ |
| 2 | Secondary | $C_2H_5$ | $C_2H_5$ |
| 3 | Secondary | $C_3H_7$ (n or iso) | $C_3H_7$ (n or iso) |
| 4 | Secondary | $C_4H_9$ (n, sec, iso, or tert) | $C_4H_9$ (n, sec, iso, or tert) |
| 5 | Secondary | $C_6H_{13}$ (n or iso) | $C_6H_{13}$ (n or iso) |
| 6 | Secondary | $C_8H_{17}$ (n or 2-EtHexyl) | $C_8H_{17}$ (n or 2-EtHexyl) |
| 7 | Secondary | $C_6H_{11}$ (cyclohexyl) | $C_6H_{11}$ (cyclohexyl) |
| 8 | Secondary | $C_3H_7$ (iso) | $C_6H_{11}$ (cyclohexyl) |
| 9 | Secondary | $C_2H_5$ | $C_4H_9$ (n) |
| 10 | Secondary | $C_{10}H_{21}$ (n) | $C_{10}H_{21}$ (n) |
| 11 | Secondary | $(CH_3)_3Si$— | $(CH_3)_3Si$— |
| 12 | Secondary | $(CH_3)_3Si$— | $C_3H_7$ (iso) |
| 13 | Secondary | $(CH_3)_3Si$— | $C_4H_9$ (n) |
| 14 | Secondary | $(CH_3)_3$—C— | $C_3H_7$ (iso) |
| 15 | Primary | H | $CH_3$ |
| 16 | Primary | H | $C_2H_5$ |
| 17 | Primary | H | $C_3H_7$ (n or iso) |
| 18 | Primary | H | $C_4H_9$ (n, iso, sec or tert) |
| 19 | Primary | H | $C_6H_{13}$ (n or iso) |
| 20 | Primary | H | $C_8H_{17}$ (n or 2-EtHexyl) |
| 21 | Primary | H | $C_{10}H_{21}$ (n) |
| 22 | Primary | H | $C_6H_{11}$ (cyclohexyl) $C_5H_{11}$ (n; iso, or 2,2-Dime-1-propyl) |
| 23 | Primary | H | $C_6H_5$ (phenyl) |
| 24 | Primary | H | $C_7H_7$ tolyl |
| 25 | Secondary | $C_6H_5$ phenyl | $C_4H_9$ n-butyl |

| Comp. No. | Compound Type | $R_1$ | $R_2$ | Name of Amine |
|---|---|---|---|---|
| 26 | Secondary | $C_6H_5$ phenyl | | $C_3H_7$ isopropyl |
| 27 | Secondary | $C_6H_5$ phenyl | | $C_6H_5$ phenyl |
| 28 | Secondary | —$CH_2CH_2CH_2CH_2$— | | Pyrrolidine |
| 29 | Secondary | —$CH_2$—$CH_2$—$CH_2$—$CH_2$—$CH_2$— | | Piperidine |
| 30 | Secondary | —$CH_2$—CH=CH—$CH_2$— | | Pyrroline |
| 31 | Secondary | —$CH_2$—$CH_2O$—$CH_2$—$CH_2$— | | Morpholine |
| 32 | Secondary | —$CH_2$—$CH_2N(CH_3)$—$CH_2$—$CH_2$— | | N-Methylpiperazine |
| 33 | Secondary | —$C(CH_3)$=CH—CH=$C(CH_3)$— | | 2,5-Dimethylpyrrole |
| 34 | Secondary | —$CH(CH_3)$—$CH_2$—$CH_2$—$CH(CH_3)$— | | 2,5-Dimethylpyrrolidine |
| 35 | Secondary | —$CH(CH_3)$—$CH_2$—$CH_2$—$CH_2$—$CH(CH_3)$— | | 2,6-Dimethylpiperidine |
| 36 | Secondary | —$C(CH_3)_2$—$CH_2$—$CH_2$—$CH_2$—$C(CH_3)_2$— | | 2,2,6,6-Tetramethylpiperidine |

TABLE 2

| Example No. | Name of Amine | DBM M Moles | Amine M Moles | Solvent | Results MDA (Molarity) Concentration | Product Description |
|---|---|---|---|---|---|---|
| 4 | Di-n-butylamine | 14.4 | 29.0 | Heptane | 0.60 | Clean solution |
| 5 | Di-n-butylamine | 16.0 | 32.5 | Hexane | 0.65 | Clean solution |
| 6 | Di-n-propylamine | 14.4 | 30.0 | Heptane | 0.60 | Clean solution |
| 7 | Di-n-propylamine | 16.0 | 32.5 | Hexane | 0.65 | Clean solution |
| 8 | Dioctylamine | 14.4 | 30.0 | Heptane | 0.52 | Clean solution |
| 9 | Diamylamine | 14.4 | 30.0 | Heptane | 0.55 | Clean solution |
| 10 | Bis(2-EtHexyl) amine | 14.4 | 30.0 | Heptane | 0.50 | Clean solution |
| 11 | 2,2,6,6-Tetramethyl piperidine | 14.4 | 30.0 | Heptane | 0.67 | Clean solution |
| 12 | 1:1 mixture of di-n-butyl and propylamines | 14.4 | 30.0 | Heptane | 0.60 | Clean solution |
| 13 | 1:1 mixture of diamylamine and tetramethyl-piperidine | 14.4 | 30.0 | Heptane | 0.58 | Clean solution |
| 14 | 2,6-dimethyl-piperidine | 10.5 | 22.0 | Heptane | 0.80 | Clean solution |
| 15 | Di-n-hexylamine | 10.5 | 22.0 | Heptane | 0.70 | Clean solution |
| 16 | Hexamethyl-disilazane | 10.5 | 22.0 | Heptane | 0.70 | Clean solution, but on cooling to low temperature (<20° C.) produce crystals which dissolve on heating to |

TABLE 2-continued

| Example No. | Name of Amine | DBM M Moles | Amine M Moles | Solvent | Results MDA (Molarity) Concentration | Product Description |
|---|---|---|---|---|---|---|
| 17 | n-Isopropyl-cyclohexylamine | 10.5 | 22.0 | Heptane | 0.38 | 30° C. and/or adding THF. 50% of the total Mg is soluble as magnesium bis-n-isopropylcycto-hexylamide, 50% dropped out as white solid which is not soluble on warming. |
| 18 | Diethylamine | 21.0 | 43.5 | Heptane | Solid | White solid, insoluble on heating or in presence of excess amine. |
| 19 | Isopropylamine | 21.0 | 42.5 | Heptane | Solid | No soluble Mg, solid white precipitated out as magnesium bis-iso propylamide, not soluble on heating or excess amine. |
| 20 | 2-Ethexylamine | 21.0 | 43.0 | Heptane | Solid | No soluble Mg, solid white precipitated out as magnesium bis-2-ethylhexylamide, not soluble on heating or excess amine. |
| 21 | Pyrrolidine | 21.0 | 43.0 | Heptane | Solid | No soluble Mg, solid white precipitated out as magnesium dipyrroli-dide, not soluble on heating or excess amine. |
| 22 | 2,2-Dimethyl-1-propylamine | 21.0 | 43.0 | Heptane | Solid | No soluble Mg, solid white precipitated out as magnesium bis-2,2-dimethyl-1-propylamide, not soluble on heating or excess amine. |
| 23 | n-Butylamine | 21.0 | 43.0 | Heptane | Solid | No soluble Mg, solid white precipitated out as magnesium bis-n-butylamide, not soluble on heating or excess amine. |

What is claimed is:

1. An ether-free lithium magnesium diorganoamide comprising a composition represented by the formula:

$$Li_xMg_y(NR^3R^4)_z$$

wherein $R^3$ and $R^4$ are independently selected from the group of hydrogen, primary, secondary and tertiary alkyl groups containing 2 to 20 carbon atoms, cycloalkyl groups containing 3 to 20 carbon atoms and aryl groups containing 6 to 10 carbon atoms, $x+y=1$ and $z=x+2y$ with the proviso that at least one of $R^3$ and $R^4$ is other than hydrogen and $R^3$ and $R^4$ are not both hydrogen.

2. The composition of claim 1 in which $R^3$ and $R^4$ are the same and selected from primary, secondary and tertiary alkyl groups of 2 to 20 carbon atoms, cycloalkyl groups of 3 to 20 carbon atoms and aryl groups of 6 to 10 carbon atoms.

3. The composition of claim 1 in which $R^3$ and $R^4$ are different and selected from primary, secondary and tertiary alkyl groups containing 2 to 20 carbon atoms, cycloalkyl groups containing 3 to 20 carbon atoms and aryl groups containing 6 to 10 carbon atoms.

4. A composition according to claim 1 additionally comprising a liquid hydrocarbon solvent.

* * * * *

UNITED STATES PATENT AND TRADEMARK OFFICE
CERTIFICATE OF CORRECTION

PATENT NO. : 4,944,894
DATED : July 31, 1990
INVENTOR(S) : Vijay C. Mehta, Terry L. Rathman, Ramiro Sanchez, and Robert C. Morrison It is certified that error appears in the above-identified patent and that said Letters Patent is hereby corrected as shown below:

On the cover page, "Lithium Corporatoin" should read --Lithium Corporation--. Column 4, line 64, "$Li_{0.99}Mg_{0.01}(NR^3R^4)_{0.01}$" should read --$Li_{0.99}Mg_{0.01}(NR^3R^4)_{1.01}$--. Column 6, line 5, "x 32 2 and v = 1" should read --x = 2 and y = 1--. Column 6, line 37, "cyclicamines" should read --cyclic amines--. Column 9, line 6, "nheptane" should read --n-heptane--. Column 9, line 20, "llask" should read --flask--. Column 10, line 41, "30° $\pm$ 35°C" should read --30°-35°C--. Column 10, line 56, "buitylamine" should read --butylamine--; and line 62, "(55 ° -60 ° C)" should read --(55°-60°C)--. Column 11, line 22, "soltuion" should read --solution--. Column 12, lines 30 and 56, "(3 ° $\pm$3°C)" should read --(3° $\pm$ 3°C)--. In Table 1, Comp. No. 31, "$-CH_2-CH_2O-CH_2-CH_2-$" should read -- $-CH_2-CH_2-O-CH_2-CH_2-$ --; and Comp. No. 32, "$-CH_2-CH_2N(CH_3)-CH_2-CH_2-$" should read -- $-CH_2CH_2-N(CH_3)-CH_2-CH_2-$ --. In Table 2, Example No. 17, Example 20, "2-Ethexylamine" should read --2-EtHexylamine--. Column 6, lines 11 and 27 --"v=1 and v=2, should be "y=1"--. and " y = 2"

Signed and Sealed this

Eleventh Day of July, 1995

BRUCE LEHMAN

Attest:

Attesting Officer

Commissioner of Patents and Trademarks